United States Patent
Pan et al.

(10) Patent No.: US 9,301,973 B2
(45) Date of Patent: Apr. 5, 2016

(54) METHODS AND COMPOSITIONS SUITABLE FOR PROMOTING HEALTHY SKIN

(75) Inventors: Yuanlong Pan, Chesterfield, MO (US); Steven Scott Hannah, Chesterfield, MO (US); Rondo Paul Middleton, Creve Coeur, MO (US)

(73) Assignee: Nestec S.A., Vevey (CH)

(*) Notice: Subject to any disclaimer, the term of this patent is extended or adjusted under 35 U.S.C. 154(b) by 3 days.

(21) Appl. No.: 13/881,507

(22) PCT Filed: Oct. 21, 2011

(86) PCT No.: PCT/US2011/001795
§ 371 (c)(1),
(2), (4) Date: Apr. 25, 2013

(87) PCT Pub. No.: WO2012/057824
PCT Pub. Date: May 3, 2012

(65) Prior Publication Data
US 2013/0209583 A1    Aug. 15, 2013

Related U.S. Application Data

(60) Provisional application No. 61/455,841, filed on Oct. 27, 2010.

(51) Int. Cl.
| | |
|---|---|
| A61K 33/04 | (2006.01) |
| A61K 33/30 | (2006.01) |
| A61K 8/41 | (2006.01) |
| A61Q 19/00 | (2006.01) |
| A61K 8/31 | (2006.01) |
| A61K 8/64 | (2006.01) |
| A61K 8/67 | (2006.01) |
| A61Q 19/06 | (2006.01) |
| A61Q 19/08 | (2006.01) |
| A61K 8/97 | (2006.01) |
| A61K 8/19 | (2006.01) |
| A61K 31/01 | (2006.01) |
| A61K 31/015 | (2006.01) |
| A61K 31/341 | (2006.01) |
| A61K 31/355 | (2006.01) |
| A61K 45/06 | (2006.01) |
| A61K 9/00 | (2006.01) |

(52) U.S. Cl.
CPC . *A61K 33/04* (2013.01); *A61K 8/19* (2013.01); *A61K 8/31* (2013.01); *A61K 8/416* (2013.01); *A61K 8/645* (2013.01); *A61K 8/678* (2013.01); *A61K 8/97* (2013.01); *A61K 9/0014* (2013.01); *A61K 31/01* (2013.01); *A61K 31/015* (2013.01); *A61K 31/341* (2013.01); *A61K 31/355* (2013.01); *A61K 45/06* (2013.01); *A61Q 19/06* (2013.01); *A61Q 19/08* (2013.01); *A61K 2800/522* (2013.01)

(58) Field of Classification Search
USPC ............................ 424/702, 725; 33/702, 725
See application file for complete search history.

(56) References Cited

U.S. PATENT DOCUMENTS

| | | | | |
|---|---|---|---|---|
| 5,128,334 | A * | 7/1992 | Nishikawa et al. | 514/159 |
| 5,602,183 | A * | 2/1997 | Martin et al. | 514/724 |
| 5,997,852 | A * | 12/1999 | Yoneda et al. | 424/70.1 |
| 6,271,254 | B1* | 8/2001 | Ulrich et al. | 514/440 |
| 6,887,497 | B2* | 5/2005 | Gorsek | 424/725 |
| 6,932,987 | B1* | 8/2005 | Diaz et al. | 424/725 |
| 2005/0226945 | A1 | 10/2005 | Ruwart | |
| 2006/0216251 | A1 | 9/2006 | Morariu | |
| 2007/0231371 | A1* | 10/2007 | Pan et al. | 424/442 |
| 2008/0033027 | A1 | 2/2008 | Bascomb et al. | |
| 2008/0241226 | A1 | 10/2008 | Abeln et al. | |
| 2010/0272790 | A1 | 10/2010 | Morariu | |

FOREIGN PATENT DOCUMENTS

| | | |
|---|---|---|
| WO | 03047596 | 6/2003 |
| WO | 2004096119 | 11/2004 |
| WO | 2005074719 | 8/2005 |

OTHER PUBLICATIONS

Written Opinion and International Search Report, PCT/US11/01795, dated Feb. 29, 2012.
Supplemental European Search Report, EP11836756.4, dated Feb. 4, 2014.

* cited by examiner

*Primary Examiner* — Gina Justice
(74) *Attorney, Agent, or Firm* — Ronald A. Burchett; Julie M. Lappin

(57) ABSTRACT

The invention provides methods, compositions, and dietary formulations useful for preventing or treating dermatitis, promoting healthy skin, and retarding skin aging. The methods comprise administering to an animal a therapeutically effective amount of a combination of at least two of one or more antioxidants; one or more anti-glycation agents; one or more body fat reducing agents; one or more insulin sensitivity enhancing agents; and one or more anti-inflammatory agents.

6 Claims, No Drawings

METHODS AND COMPOSITIONS SUITABLE FOR PROMOTING HEALTHY SKIN

CROSS REFERENCE TO RELATED APPLICATIONS

This application is a national stage application under 35 USC §371 of PCT/US2011/001795 filed on 21 Oct. 2011 and claims priority to U.S. Provisional Application No. 61/455,841 filed 27 Oct. 2010, the disclosures of which are incorporated herein by this reference.

BACKGROUND OF THE INVENTION

1. Field of the Invention

The invention relates generally to healthy skin and particularly to methods and compositions for preventing or treating dermatitis, promoting healthy skin, and retarding skin aging.

2. Description of Related Art

The skin is the largest organ of the body and therefore critical to good health. Skin health is affected by aging and by various disease and conditions, e.g., dermatitis. Preventing or treating dermatitis, promoting healthy skin, and retarding skin aging are common problems that may require medical intervention but are better managed using preventive skin care.

Dermatitis is an inflammation of the skin. The word "dermatitis" is used to describe a number of different skin disorders that are caused by infections, allergies, and irritating substances. The term may also be used to refer to atopic dermatitis, commonly known as eczema. The rashes range from mild to severe and include symptoms, depending on their cause, such as itchiness, painful ulcers, reddening, thickening, swelling, marking, crusting, scaling, creasing, blisters, or other changes in the normal condition of the skin. The treatment of dermatitis varies greatly and is determined by the cause. Common treatments include cortisone-type creams, antihistamines and avoidance of the allergen or irritant. Typically, dermatitis is not life-threatening or contagious but it often causes embarrassment and can create severe discomfort and pain. Dermatitis may lead to complications such as Impetigo and cellulitis. Other potential complications include scaring and changes in skin color.

Many treatments for promoting healthy skin and treating skin disease are known but none have proven to be completely effective. There is, therefore, a need for methods and compositions useful for preventing or treating dermatitis, promoting healthy skin, and retarding skin aging.

SUMMARY OF THE INVENTION

It is, therefore, an object of the present invention to provide methods and dietary formulations useful for preventing or treating dermatitis, promoting healthy skin, and retarding skin aging.

It is another object of the invention to provide methods and dietary formulations for promoting the health and wellness of animals.

It is yet another object of the present invention to provide methods and dietary formulations for extending the prime years of an animal's life.

One or more of these or other objects are achieved by administering to an animal a therapeutically effective amount of a combination of at least two of: one or more antioxidants; one or more anti-glycation agents; one or more body fat reducing agents; one or more insulin sensitivity enhancing agents; and one or more anti-inflammatory agents.

Other and further objects, features, and advantages of the present invention will be readily apparent to those skilled in the art.

DETAILED DESCRIPTION OF THE INVENTION

Definitions

The term "animal" means any animal that has a need for preventing or treating dermatitis, promoting healthy skin, retarding skin aging in an animal, including human, avian, bovine, canine, equine, feline, hicrine, lupine, murine, ovine, or porcine animals.

The term "companion animal" means domesticated animals such as cats, dogs, rabbits, guinea pigs, ferrets, hamsters, mice, gerbils, horses, cows, goats, sheep, donkeys, pigs, and the like.

The term "therapeutically-effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treating", "treat", and "treatment" embrace both preventative, i.e., prophylactic, and palliative treatment.

The terms "pharmaceutically acceptable" and "nutraceutically acceptable" indicates that the substance or composition must be compatible chemically and/or toxicologically, with the other ingredients comprising a formulation, and/or the mammal being treated therewith.

The term "health and/or wellness of an animal" means the complete physical, mental, and social well being of the animal, not merely the absence of disease or infirmity.

The term "extending the prime" means extending the number of years an animal lives a healthy life and not just extending the number of years an animal lives, e.g., an animal would be healthy in the prime of its life for a relatively longer time.

The term "in conjunction" means that compositions of the invention are administered to an animal (1) together in a food composition or (2) separately at the same or different frequency using the same or different administration routes at about the same time or periodically. "Periodically" means that compositions are administered on a schedule acceptable for specific compounds or compositions. "About the same time" generally means that compositions are administered at the same time or within about 72 hours of each other.

The term "dietary supplement" means a product that is intended to be ingested in addition to a normal animal diet. Dietary supplements may be in any form, e.g., solid, liquid, gel, tablet, capsule, powder, and the like. Preferably they are provided in convenient dosage forms, e.g., in sachets. Dietary supplements can be provided in bulk consumer packages such as bulk powders, liquids, gels, or oils. Similarly such supplements can be provided in bulk quantities to be included in other food items such as snacks, treats, supplement bars, beverages, and the like.

The term "dermatitis" refers to any inflammation of the skin. Types of dermatitis include, but are not limited to, actinic dermatitis, allergic dermatitis including atopic dermatitis and allergic contact dermatitis, ammonia dermatitis, atopic dermatitis, berlock dermatitis, berloque dermatitis, cercarial dermatitis (swimmer's itch), contact dermatitis, diaper dermatitis (diaper rash), dermatitis exfoliati'va neonato'rum (staphylococcal scalded skin syndrome), exfoliative dermatitis, dermatitis herpetifor'mis, infectious eczematous dermatitis, insect dermatitis, irritant dermatitis, livedoid dermatitis, meadow dermatitis, meadow-grass dermatitis (phytophotodermatitis), dermatitis medicamentosa, perioral dermatitis, photoallergic contact dermatitis, photocontact dermatitis, phototoxic dermatitis, poison ivy dermatitis, poison oak dermatitis, poison sumac dermatitis, radiation dermatitis (radiodermatitis), rat mite dermatitis, dermatitis re'pens (acrodermatitis continua), rhus dermatitis (poison ivy, poison oak, or poison sumac dermatitis), schistosome dermatitis (swimmer's itch), seborrheic dermatitis, dermatitis seborrhe'ica, stasis dermatitis, uncinarial dermatitis (ground itch), dermatitis venenata, and x-ray dermatitis (radiodermatitis).

The term "aging" means being of an advanced age such that an animal has reached or exceeded 50% of the average life expectancy for the animal's species and/or breed within such species. For example, if the average life expectancy for a given breed of dog is 12 years, then an "aging animal" within that breed is 6 years old or older.

The term "food" or "food product" or "food composition" means a product or composition that is intended for ingestion by an animal, including a human, and provides nutrition to the animal.

The term "regular basis" means at least monthly dosing with dietary formulations of the present invention and more preferably weekly dosing. More frequent dosing or consumption, such as twice or three times weekly, is preferred in certain embodiments. Still more preferred are regimens that comprise at least once daily consumption, e.g., when dietary formulations of the present invention are a component of a food composition that is consumed at least once daily.

The term "single package" means that the components of a kit are physically associated in or with one or more containers and considered a unit for manufacture, distribution, sale, or use. Containers include, but are not limited to, bags, boxes, cartons, bottles, packages such as shrink wrap packages, stapled or otherwise affixed components, or combinations thereof. A single package may be containers of individual dietary formulations of the present invention and food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The dosages expressed herein are in milligrams per kilogram of body weight per day (mg/kg/day) unless expressed otherwise.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a supplement", "a method", or "a food" includes a plurality of such "supplements", "methods", or "foods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

The Invention

In one aspect, the invention provides methods for preventing or treating dermatitis in an animal. The methods comprise administering to the animal a therapeutically effective amount of a combination of at least two of one or more antioxidants; one or more anti-glycation agents; one or more body fat reducing agents; one or more insulin sensitivity enhancing agents; and one or more anti-inflammatory agents. In preferred embodiments, the combination is administered as a dietary formulation.

In another aspect, the invention provides methods for promoting healthy skin in an animal. The methods comprise administering to the animal a therapeutically effective amount of a combination of at least two of one or more antioxidants; one or more anti-glycation agents; one or more body fat reducing agents; one or more insulin sensitivity enhancing agents; and one or more anti-inflammatory agents. In preferred embodiments, the combination is administered as a dietary formulation.

In another aspect, the invention provides methods for retarding skin aging in an animal. The methods comprise administering to the animal a therapeutically effective amount of a combination of at least two of one or more antioxidants; one or more anti-glycation agents; one or more body fat reducing agents; one or more insulin sensitivity enhancing agents; and one or more anti-inflammatory agents. In preferred embodiments, the combination is administered as a dietary formulation.

In another aspect, the invention provides dietary formulations suitable for preventing or treating dermatitis, promoting healthy skin, and retarding skin aging in an animal. The dietary formulations comprises a combination of at least two of one or more antioxidants; one or more anti-glycation agents; one or more body fat reducing agents; one or more insulin sensitivity enhancing agents; and one or more anti-inflammatory agents.

The inventions are based upon the discovery that animals who were fed the dietary formulations of the present invention demonstrated an improvement in the incidence of dermatitis. The methods and compositions of the present invention may also be useful in the treatment of promoting healthy skin and retarding skin aging.

In some embodiments, the antioxidants are selected from the group consisting of vitamin C, polyphenols, proanthocyanidins, anthocyanins, bioflavonoids, selenium, alpha-lipoic acid, glutathione, catechin, epicatechin, epigallocatechin, epigallocatechin gallate, epicatechin gallate, cysteine, vitamin E, gamma tocopherol, alpha-carotene, beta-carotene, lutein, zeaxanthin, retinal, astaxanthin, cryptoxanthin, natural mixed carotenoids, lycopene and resveratrol. In a preferred embodiment, the antioxidants are selected from the group consisting of vitamin E, vitamin C, selenium, lycopene, and carotenoids.

In some embodiments, the antioxidants are administered to the animal in amounts of from about 0.001 to about 1000 mg/kg/day, preferably from about 0.01 to 500, more preferably from about 0.1 to about 250. In another embodiment, the antioxidants are administered to the animal in amounts of from about 0.001 to about 10 grams day, preferably from about 0.01 to 8, more preferably from about 0.12 to about 5.

In some embodiments, the anti-glycation agents are selected from the group consisting of carnosine, benfotiamine, pyridoxamine, alpha-lipoic acid, phenacyldimethylthiazolium chloride, taurine, aminoguanidine, resveratrol, and aspirin. In a preferred embodiment, the anti-glycation agent is carnosine.

In some embodiments, the anti-glycation agents are administered to the animal in amounts of from about 0.01 to about 1000 mg/kg/day, preferably from about 1 to 500, more preferably from about 10 to about 100. In another embodiment, the antioxidants are administered to the animal in amounts of from about 0.001 to about 10 grams day, preferably from about 0.01 to 8, more preferably from about 0.1 to about 5.

In some embodiments, body fat reducing agents are selected from the group consisting of conjugated linoleic acid (CLA), carnitine, acetyl-carnitine, pyruvate, polyunsaturated fatty acids, medium chain fatty acids, medium chain triglycerides, and soy isoflavones. In a preferred embodiment, the body fat reducing agents are selected from the group consisting of conjugated linoleic acid (CLA), carnitine, and acetyl-carnitine.

In some embodiments, the body fat reducing agents are administered to the animal in amounts of from about 0.001 to about 1000 mg/kg/day, preferably from about 0.01 to 500, more preferably from about 0.1 to about 250. In another embodiment, the antioxidants are administered to the animal in amounts of from about 0.001 to about 10 grams day, preferably from about 0.01 to 8, more preferably from about 0.1 to about 5.

In some embodiments, insulin sensitivity enhancing agents are selected from the group consisting of chromium, chromium picolinate, cinnamon, cinnamon extract, polyphenols from cinnamon and witch hazel, coffee berry extract, chlorogenic acid, caffeic acid, a source of zinc, and grape seed extract. In a preferred embodiment, the insulin sensitivity enhancing agents are selected from the group consisting of chromium picolinate, zinc sulfate, zinc monomethionate, and grape seed extract.

In some embodiments, the insulin sensitivity enhancing agents are administered to the animal in amounts of from about 0.001 to about 1000 mg/kg/day, preferably from about 0.01 to 500, more preferably from about 0.1 to about 250. In another embodiment, the antioxidants are administered to the animal in amounts of from about 0.001 to about 10 grams day, preferably from about 0.01 to 8, more preferably from about 0.1 to about 5.

In some embodiments, anti-inflammatory agents are selected from the group consisting of omega-3 fatty acids and curcumin. In some embodiments, the omega-3 fatty acids are selected from the group consisting of α-linolenic acid, eicosapentaenoic acid, docosapentaenoic acid, docosahexaenoic acid, flax seed, flax oil, walnuts, canola oil, wheat germ, and fish oil. In some embodiments, the source of curcumin is selected from the group consisting of (1,7-bis-(4-hydroxy-3-methoxyphenyl)-hepta-1,6-diene-3,5-dione; 1-(4-hydroxyphenyl)-7-(4-hydroxy-3-methoxyphenyl)-hepta-1,6-diene-3,5-dione; 1,7-bis-(4-hydroxyphenyl)-hepta-1,6-diene-3,5-dione), demethoxycurcumin, and bis-demethoxycurcumin.

In some embodiments, the anti-inflammatory agents are administered to the animal in amounts of from about 0.001 to about 1000 mg/kg/day, preferably from about 0.01 to 500, more preferably from about 0.1 to about 250. In another embodiment, the antioxidants are administered to the animal in amounts of from about 0.001 to about 10 grams day, preferably from about 0.01 to 8, more preferably from about 0.1 to about 5.

In one embodiment, the dietary formulation comprises one or more antioxidants.

In another embodiment, the dietary formulation comprises a combination of: one or more antioxidants; one or more anti-glycation agents; one or more body fat reducing agents; andone or more insulin sensitivity enhancing agents.

In another embodiment, the dietary formulation comprises vitamin E, vitamin C, alpha-carotene, beta-carotene, lutein, zeaxanthin, cryptoxanthin, selenium, lycopene, chromium, grape seed extract, zinc, CLA, carnitine, acetyl-carnitine, and carnosine.

In one embodiment, the dietary formulation comprises a combination of: one or more antioxidants; one or more anti-glycation agents; one or more body fat reducing agents; one or more insulin sensitivity enhancing agents; and one or more anti-inflammatory agents.

In another embodiment, the dietary formulation comprises vitamin E, vitamin C, alpha-carotene, beta-carotene, lutein, zeaxanthin, cryptoxanthin, selenium, lycopene, chromium, grape seed extract, zinc, CLA, carnitine, acetyl-carnitine, carnosine, fish oil, and curcumin.

In one embodiment, the dietary formulation comprises a combination of: one or more antioxidants and one or more anti-inflammatory agents.

In another embodiment the dietary formulation comprises vitamin E, vitamin C, alpha-carotene, beta-carotene, lutein, zeaxanthin, cryptoxanthin, selenium, lycopene, fish oil, and curcumin.

In the methods of the invention, dietary formulations are administered to an animal in amounts of from about 0.005 to about 1000 mg/kg/day, preferably from about 0.01 to about 500 mg/kg/day, most preferably from about 0.05 to about 250 mg/kg/day.

Dietary formulations of the present invention can be administered to the animal in any suitable form using any suitable administration route. For example, the dietary formulations can be administered in a dietary formulation composition, in a food composition, in a dietary supplement, in a pharmaceutical composition, in a nutraceutical composition, or as a medicament. Similarly, the dietary formulations can be administered using a variety of administration routes, including oral, intranasal, intravenous, intramuscular, intragastric, transpyloric, subcutaneous, rectal, and the like. Preferably, the dietary formulations are administered to an animal orally. Most preferably, the dietary formulations are administered orally to an animal as a dietary supplement or as an ingredient in a food composition.

In a preferred embodiment, the dietary formulations are administered to an animal as an ingredient in a food composition suitable for consumption by an animal, including humans and companion animals such as dogs and cats. Such compositions include complete foods intended to supply the necessary dietary requirements for an animal or food supplements such as animal treats.

In various embodiments, food compositions such as pet food compositions or pet treat compositions comprise from about 5% to about 50% crude protein. The crude protein material may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof.

The food compositions may further comprise from about 5% to about 40% fat. Examples of suitable fats include animal fats and vegetable fats. Preferably the fat source is an animal fat source such as tallow or grease. Vegetable oils such as corn oil, sunflower oil, safflower oil, rape seed oil, soy bean oil, olive oil and other oils rich in monounsaturated and polyunsaturated fatty acids, may also be used.

The food compositions may further comprise from about 10% to about 60% carbohydrate. Examples of suitable carbohydrates include grains or cereals such as rice, corn, millet, sorghum, alfalfa, barley, soybeans, canola, oats, wheat, rye, triticale and mixtures thereof. The compositions may also optionally comprise other materials such as dried whey and other dairy by-products.

The moisture content for such food compositions varies depending on the nature of the food composition. The food compositions may be dry compositions (e.g., kibble), semi-moist compositions, wet compositions, or any mixture thereof. In a preferred embodiment, the composition is a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one preferred embodiment, the compositions have moisture content from about 5% to about 20%. Dry food products include a variety of foods of various moisture contents, such that they are relatively shelf-stable and resistant to microbial or fungal deterioration or contamination. Also preferred are dry food compositions that are extruded food products such as pet foods or snack foods for either humans or companion animals.

The food compositions may also comprise one or more fiber sources. The term "fiber" includes all sources of "bulk" in the food whether digestible or indigestible, soluble or insoluble, fermentable or nonfermentable. Preferred fibers are from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present invention to the immune system of an animal.

In some embodiments, the ash content of the food composition ranges from less than 1% to about 15%, preferably from about 5% to about 10%.

In a preferred embodiment, the composition is a food composition comprising the dietary formulations and from about 15% to about 50% protein, from about 5% to about 40% fat, from about 5% to about 10% ash content, and having a moisture content of about 5% to about 20%. In other embodiments, the food composition further comprises prebiotics or probiotics as described herein.

When administered in a food composition, the dietary formulations comprise from about 0.1 to about 40% of the food composition, preferably from about 3 to about 30%, more preferably from about 5 to about 20%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, or 40%.

In another embodiment, the dietary formulations are administered to an animal in a dietary supplement. The dietary supplement can have any suitable form such as a gravy, drinking water, beverage, yogurt, powder, granule, paste, suspension, chew, morsel, treat, snack, pellet, pill, capsule, tablet, sachet, or any other suitable delivery form. The dietary supplement can comprise the dietary formulations and optional compounds such as vitamins, preservatives, probiotics, prebiotics, and antioxidants. This permits the supplement to be administered to the animal in small amounts, or in the alternative, can be diluted before administration to an animal. The dietary supplement may require admixing with a food composition or with water or other diluent prior to administration to the animal. When administered in a dietary supplement, the dietary formulations comprise from about 0.1 to about 90% of the supplement, preferably from about 3 to about 70%, more preferably from about 5 to about 60%.

In another embodiment, the dietary formulations are administered to an animal in a pharmaceutical or nutraceutical composition. The pharmaceutical composition comprises the dietary formulations and one or more pharmaceutically or nutraceutically acceptable carriers, diluents, or excipients. Generally, pharmaceutical compositions are prepared by admixing a compound or composition with excipients, buffers, binders, plasticizers, colorants, diluents, compressing agents, lubricants, flavorants, moistening agents, and the like, including other ingredients known to skilled artisans to be useful for producing pharmaceuticals and formulating compositions that are suitable for administration to an animal as pharmaceuticals. When administered in a pharmaceutical or nutraceutical composition, the dietary formulations comprise from about 0.1 to about 90% of the composition, preferably from about 3 to about 70%, more preferably from about 5 to about 60%.

The dietary formulations of the present invention can be administered to the animal on an as-needed, on an as-desired basis, or on a regular basis. A goal of administration on a regular basis is to provide the animal with a regular and consistent dose of the dietary formulations or the direct or indirect metabolites that result from such ingestion. Such regular and consistent dosing will tend to create constant blood levels of the dietary formulations and their direct or indirect metabolites. Thus, administration on a regular basis can be once monthly, once weekly, once daily, or more than once daily. Similarly, administration can be every other day, week, or month, every third day, week, or month, every fourth day, week, or month, and the like. Administration can be multiple times per day. When utilized as a supplement to ordinary dietetic requirements, the dietary formulations may be administered directly to the animal, e.g., orally or otherwise. The dietary formulations can alternatively be contacted with, or admixed with, daily feed or food, including a fluid, such as drinking water, or an intravenous connection for an animal that is receiving such treatment. Administration can also be carried out as part of a dietary regimen for an animal. For example, a dietary regimen may comprise causing the regular ingestion by the animal of the dietary formulations in an amount effective to accomplish the methods of the present invention.

According to the methods of the invention, administration of the dietary formulations, including administration as part of a dietary regimen, can span a period ranging from parturition through the adult life of the animal. In various embodiments, the animal is a human or companion animal such as a dog or cat. In certain embodiments, the animal is a young or growing animal. In more preferred embodiments, the animal is an aging animal. In other embodiments administration begins, for example, on a regular or extended regular basis, when the animal has reached more than about 30%, 40%, or 50% of its projected or anticipated lifespan. In some embodiments, the animal has attained 40, 45, or 50% of its anticipated lifespan. In yet other embodiments, the animal is older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

The dietary formulations of the present invention are administered to an animal for a time required to accomplish one or more objectives of the invention, e.g., preventing or treating dermatitis; promoting healthy skin; retarding skin aging; improving the quality of life; and promoting the health and wellness in an animal. Preferably, the dietary formulations are administered to an animal on a regular basis.

In another aspect, the invention provides compositions comprising the dietary formulations in a therapeutically effective amount for one or more of preventing or treating dermatitis; promoting healthy skin; retarding skin aging; improving the quality of life in an animal; and promoting the health and wellness in an animal. The compositions contain the dietary formulations in amounts sufficient to administer the dietary formulations to an animal in amounts of from about 0.005 to about 100 mg/kg/day, preferably from about 0.01 to about 50 mg/kg/day, most preferably from about 0.05 to about 10 mg/kg/day when the compositions are administered as anticipated or recommended for a particular composition. Typically, the dietary formulations comprise from about 1 to about 90% of a composition, preferably from about 3 to about 70%, more preferably from about 5 to about 60%. In various embodiments, food compositions comprise about 1%, 2%, 4%, 6%, 8%, 10%, 12%, 14%, 16%, 18%, 20%, 22%, 24%, 26%, 28%, 30%, 32%, 34%, 36%, 38%, 40%, 45%, 50%, 55%, 60%, 70%, or 80%.

Compositions comprising the dietary formulations such as food, dietary, pharmaceutical, and other compositions may further comprise one or more substances such as vitamins, minerals, probiotics, prebiotics, salts, and functional additives such as palatants, colorants, emulsifiers, and antimicrobial or other preservatives. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat soluble vitamins as A, D, E, and K. Inulin, amino acids, enzymes, coenzymes, and the like may be useful to include in various embodiments.

In various embodiments, the compositions comprising the dietary formulations contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the compositions comprising the dietary formulations (e.g., uniformly or non-uniformly distributed in the compositions) or applied to the compositions comprising the dietary formulations (e.g., topically applied with or without a carrier). Such methods are known to skilled artisans, e.g., U.S. Pat. No. 5,968,569 and related patents.

Typical probiotics include, but are not limited to, probiotic strains selected from *Lactobacilli*, *Bifidobacteria*, or *Enterococci*, e.g., *Lactobacillus reuteii*, *Lactobacillus acidophilus*, *Lactobacillus animalis*, *Lactobacillus ruminis*, *Lactobacillus johnsonii*, *Lactobacillus casei*, *Lactobacillus paracasei*, *Lactobacillus rhamnosus*, *Lactobacillus fermentum*, and *Bifidobacterium* sp., *Enterococcus faecium* and *Enterococcus* sp. In some embodiments, the probiotic strain is selected from the group consisting of *Lactobacillus reuteri* (NCC2581; CNCM 1-2448), *Lactobacillus reuteri* (NCC2592; CNCM 1-2450), *Lactobacillus rhamnosus* (NCC2583; CNCM 1-2449), *Lactobacillus reuteri* (NCC2603; CNCM 1-2451), *Lactobacillus reuteri* (NCC2613; CNCM 1-2452), *Lactobacillus acidophilus* (NCC2628; CNCM 1-2453), *Bifidobacterium adolescentis* (e.g. NCC2627), *Bifidobacterium* sp. NCC2657 or *Enterococcus faecium* SF68 (NCIMB 10415). The compositions comprising the dietary formulations contain probiotics in amounts sufficient to supply from about $10^4$ to about $10^{12}$ cfu/animal/day, preferably from $10^5$ to about $10^{11}$ cfu/animal/day, most preferably from $10^7$ to $10^{10}$ cfu/animal/day. When the probiotics are killed or inactivated, the amount of killed or inactivated probiotics or their components should produce a similar beneficial effect as the live microorganisms. Many such probiotics and their benefits are known to skilled artisans, e.g., EP1213970B1, EP1143806B1, U.S. Pat. No. 7,189,390, EP1482811B1, EP1296565B1, and U.S. Pat. No.

6,929,793. In a preferred embodiment, the probiotic is *Enterococcus faecium* SF68 (NCIMB 10415). In one embodiment, the probiotics are encapsulated in a carrier using methods and materials known to skilled artisans.

As stated, the compositions comprising the dietary formulations may contain one or more prebiotics, e.g., facto-oligosaccharides, gluco-oligosaccharides, galacto-oligosaccharides, isomalto-oligosaccharides, xylo-oligosaccharides, soybean oligosaccharides, lactosucrose, lactulose, and isomaltulose. In one embodiment, the prebiotic is chicory root, chicory root extract, inulin, or combinations thereof. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package. Typically, the food composition contains from about 0.1 to about 10% prebiotic, preferably from about 0.3 to about 7%, most preferably from about 0.5 to 5%, on a dry matter basis. The prebiotics can be integrated into the compositions using methods known to skilled artisans, e.g., U.S. Pat. No. 5,952,033.

A skilled artisan can determine the appropriate amount of the dietary formulations, food ingredients, vitamins, minerals, probiotics, prebiotics, antioxidants, or other ingredients to be use to make a particular composition to be administered to a particular animal. Such artisan can consider the animal's species, age, size, weight, health, and the like in determining how best to formulate a particular composition comprising the dietary formulations and other ingredients. Other factors that may be considered include the type of composition (e.g., pet food composition versus dietary supplement), the desired dosage of each component, the average consumption of specific types of compositions by different animals (e.g., based on species, body weight, activity/energy demands, and the like), and the manufacturing requirements for the composition.

In a further aspect, the invention provides kits suitable for administering the dietary formulations to animals. The kits comprise in separate containers in a single package or in separate containers in a virtual package, as appropriate for the kit component, the dietary formulations and one or more of (1) one or more ingredients suitable for consumption by an animal; (2) instructions for how to combine the dietary formulations and other kit components to produce a composition useful for preventing or treating dermatitis, promoting healthy skin, and retarding skin aging; (3) instructions for how to use the dietary formulations for preventing or treating dermatitis (4) instructions for how to use the dietary formulations for promoting healthy skin; (5) instructions for how to use the dietary formulations for retarding skin aging; (6) one or more probiotics; (7) one or more inactivated probiotics; (8) one or more components of inactivated probiotics that promote health benefits similar to or the same as the probiotics, e.g., proteins, lipids, glycoproteins, and the like; (9) one or more prebiotics; (10) a device for preparing or combining the kit components to produce a composition suitable for administration to an animal; and (11) a device for administering the combined or prepared kit components to an animal. In one embodiment, the kit comprises the dietary formulations and one or more ingredients suitable for consumption by an animal. In another embodiment, the kit comprises instructions for how to combine the dietary formulations and the ingredients to produce a composition useful for preventing or treating dermatitis, promoting healthy skin, and retarding skin aging. In one embodiment, the kit comprises the dietary formulation in a sachet.

When the kit comprises a virtual package, the kit is limited to instructions in a virtual environment in combination with one or more physical kit components. The kit contains the dietary formulations and other components in amounts sufficient for preventing or treating dermatitis, promoting healthy skin, and retarding skin aging. Typically, the dietary formulations and the other suitable kit components are admixed just prior to consumption by an animal. The kits may contain the kit components in any of various combinations and/or mixtures. In one embodiment, the kit contains a packet containing the dietary formulations and a container of food for consumption by an animal. The kit may contain additional items such as a device for mixing the dietary formulations and ingredients or a device for containing the admixture, e.g., a food bowl. In another embodiment, the dietary formulations are mixed with additional nutritional supplements such as vitamins and minerals that promote good health in an animal. The components are each provided in separate containers in a single package or in mixtures of various components in different packages. In preferred embodiments, the kits comprise the dietary formulations and one or more other ingredients suitable for consumption by an animal. Preferably such kits comprise instructions describing how to combine the dietary formulations with the other ingredients to form a food composition for consumption by the animal, generally by mixing the dietary formulations with the other ingredients or by applying the dietary formulations to the other ingredients, e.g., by sprinkling the dietary formulations on a food composition.

In a further aspect, the invention provides a means for communicating information about or instructions for one or more of (1) using the dietary formulations for preventing or treating dermatitis; (2) using the dietary formulations for promoting healthy skin; (3); using the dietary formulations for retarding akin aging; (4) contact information for consumers to use if they have a question regarding the methods and compositions of the invention; and (5) nutritional information about the dietary formulations. The communication means is useful for instructing on the benefits of using the invention and communicating the approved methods for administering the dietary formulations and food compositions containing the dietary formulations to an animal. The means comprises one or more of a physical or electronic document, digital storage media, optical storage media, audio presentation, audiovisual display, or visual display containing the information or instructions. Preferably, the means is selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, the invention provides methods for manufacturing a food composition comprising the dietary formulations and one or more other ingredients suitable for consumption by an animal, e.g., one or more of protein, fat, carbohydrate, fiber, vitamins, minerals, probiotics, prebiotics, and the like. The methods comprise admixing one or more ingredients suitable for consumption by an animal with the dietary formulations. Alternatively, the methods comprise applying the dietary formulations alone or in conjunction or combination with other ingredients onto the food composition, e.g., as a coating or topping. The dietary formulations can be added at any time during the manufacture and/or processing of the food composition. The composition can be made according to any method suitable in the art.

In another aspect, the invention provides a package useful for containing the dietary formulations of the invention. The package comprises at least one material suitable for containing the dietary formulations and a label affixed to the material containing a word or words, picture, design, acronym, slogan, phrase, or other device, or combination thereof, that indicates that the package contains the dietary formulations with beneficial properties relating to the skin, e.g., dermatitis. Typically, such device comprises the words "preventing dermatitis," "treating dermatitis," "promoting healthy skin" and "retarding skin aging" or an equivalent expression printed on the material. Any package configuration and packaging material suitable for containing the dietary formulations are useful in the invention, e.g., a bag, box, bottle, can, pouch, and the like manufactured from paper, plastic, foil, metal, and the like. In preferred embodiments, the package further comprises the dietary formulations of the invention. In various embodiments, the package further comprises at least one window that permit the package contents to be viewed without opening the package. In some embodiments, the window is a transparent portion of the packaging material. In others, the window is a missing portion of the packaging material. In a preferred embodiment, the package contains a food composition adapted for a particular animal such as a human, canine, or feline, as appropriate for the label, preferably a companion animal food composition for dogs or cats. In a preferred embodiment, the package is a can or pouch comprising a food composition of the invention.

In another aspect, the invention provides for use of the dietary formulations to prepare a medicament for one or more of preventing or treating dermatitis; promoting healthy skin; retarding skin aging; improving the quality of life; and promoting the health and wellness in an animal. Generally, medicaments are prepared by admixing a compound or composition, i.e., the dietary formulations or a composition comprising the dietary formulations, with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

In another aspect, the invention provides methods for preventing or treating dermatitis in an animal, promoting healthy skin in an animal, and retarding skin aging in an animal. The methods comprise administering a dermatitis preventing or treating amount, a healthy skin promoting amount, or an aging skin retarding amount of at least one antioxidant to the animal. Any amount suitable for preventing or treating dermatitis in an animal, promoting healthy skin in an animal, or retarding skin aging is suitable. Generally, the antioxidants are administered in amounts of from about 1 to about 20 times the daily recommend amount for the particular antioxidant, such amount being limited to an amount that is not toxic for the animal. Preferably, the antioxidants are administered in amounts of from about 1 to about 10 times the recommended daily allowance (RDA) for the antioxidant, more preferably from about 2 to about 8 times the RDA, most preferably from about 2 to about 5 times the RDA. The antioxidants re administered using any suitable means and route for the particular antioxidant. Preferably, the antioxidants are administered orally alone, in a supplement, or as part of a comestible composition such as a food, treat, or beverage.

In another aspect, the invention provides a package useful for containing a combination of at least two of one or more antioxidants; one or more anti-glycation agents; one or more body fat reducing agents; one or more insulin sensitivity enhancing agents; and one or more anti-inflammatory agents. The package comprises at least one material suitable for containing the combination and a label affixed to the material containing a word or words, picture, design, acronym, slogan, phrase, or other device, or combination thereof, that indicates that the package contains the combination. Typically, such device comprises the words "preventing dermatitis," "treating dermatitis," "promoting healthy skin" and "retarding skin aging" or an equivalent expression printed on the material. Any package configuration and packaging material suitable for containing the combination are useful in the invention, e.g., a bag, box, bottle, can, pouch, and the like manufactured from paper, plastic, foil, metal, and the like. In preferred embodiments, the package further comprises a combination of the invention. In various embodiments, the package further comprises at least one window that permit the package contents to be viewed without opening the package. In some embodiments, the window is a transparent portion of the packaging material. In others, the window is a missing portion of the packaging material.

EXAMPLES

The invention can be further illustrated by the following examples, although it will be understood that these examples are included merely for purposes of illustration and are not intended to limit the scope of the invention unless otherwise specifically indicated.

Example 1

The feeding protocol was eleven months in duration. Fifteen month-old mice (C57Bl/6) were fed 24 grams per week of American Institute of Nutrition purified diet formula for maintenance of mature rodents (AIN-93M). There were fifteen mice in each testing group. Each group was given a supplement one of the following blends: Blend A, Blend B, Blend C, or Blend D. No supplementation was given to the control group. During the 11 months feeding trial, the skin condition of the mice was monitored and recorded. The results are shown in Table 1.

Blend A:

| Compound | Dose (mg/kg diet) |
| --- | --- |
| Vitamin E | 500 |
| Natural mixed carotenoids (alpha-carotene, beta-carotene, lutein, zeaxanthin, cryptoxanthin) | 50 |
| Selenium (L-selenomethionine, 97%) | 0.20 |
| Vitamin C | 450 |
| Lycopene | 50 |

Blend B:

| Compound | Dose (mg/kg diet) |
| --- | --- |
| Vitamin E | 500 |
| Natural mixed carotenoids (alpha-carotene, beta-carotene, lutein, zeaxanthin, cryptoxanthin) | 50 |
| Selenium (L-selenomethionine, 97%) | 0.20 |
| Vitamin C | 450 |

-continued

| Compound | Dose (mg/kg diet) |
|---|---|
| Lycopene | 50 |
| Chromium picolinate | 0.5 |
| Grape seed extract | 250 |
| Zinc monomethionine | 78 |
| CLA | 0.5% of the diet |
| Carnosine | 0.05% of the diet. |
| Carnitine | 400 |
| Acetyl-carnitine | 100 |

Blend C:

| Compound | Dose (mg/kg diet) |
|---|---|
| Vitamin E | 500 |
| Natural mixed carotenoids (alpha-carotene, beta-carotene, lutein, zeaxanthin, cryptoxanthin) | 50 |
| Selenium (L-selenomethionine, 97%) | 0.20 |
| Vitamin C | 450 |
| Lycopene | 50 |
| Fish oil | 2.65% of the diet |
| Curcumin extract | 500 |

Blend D:

| Compound | Dose (mg/kg diet) |
|---|---|
| Vitamin E | 500 |
| Natural mixed carotenoids (alpha-carotene, beta-carotene, lutein, zeaxanthin, cryptoxanthin) | 50 |
| Selenium (L-selenomethionine, 97%) | 0.20 |
| Vitamin C | 450 |
| Lycopene | 50 |
| Chromium picolinate | 0.5 |
| Grape seed extract | 250 |
| Zinc monomethionine | 78 |
| CLA | 0.5% of the diet |
| Carnosine | 0.05% of the diet. |
| Carnitine | 400 |
| Acetyl-carnitine | 100 |
| Fish oil | 2.65% of the diet |
| Curcumin extract | 500 |

TABLE 1

Dermatitis Incidence

| | Blend A | Blend B | Blend C | Blend D | Control |
|---|---|---|---|---|---|
| Number of Mice | 15 | 15 | 15 | 15 | 15 |
| Dermatitis Incident | 2 | 0 | 4 | 2 | 5 |
| Dermatitis Rate (%) | 13 | 0 | 27 | 13 | 33 |

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A method for treating dermatitis in an animal comprising administering to the animal having dermatitis a therapeutically effective amount of a combination of:
    one or more antioxidants selected from the group consisting of vitamin C, polyphenols, proanthocyanidins, anthocyanins, bioflavonoids, selenium, alpha-lipoic acid, glutathione, catechin, epicatechin, epigallocatechin, epigallocatechin gallate, epicatechin gallate, cysteine, vitamin E, gamma tocopherol, alpha-carotene, beta-carotene, lutein, zeaxanthin, retinal, astaxanthin, cryptoxanthin, lycopene and resveratrol, wherein the antioxidants are administered to the animal in amounts of from about 0.001 to about 1000 mg/kg/day;
    one or more anti-glycation agents selected from the group consisting of carnosine, benfotiamine, pyridoxamine, alpha-lipoic acid, phenacyldimethylthiazolium chloride, taurine, aminoguanidine, resveratrol, and aspirin, wherein the anti-glycation agents are administered to the animal in amounts of from about 0.01 to about 1000 mg/kg/day;
    one or more body fat reducing agents selected from the group consisting of conjugated linoleic acid (CLA), carnitine, acetyl-carnitine, pyruvate, polyunsaturated fatty acids, medium chain fatty acids, medium chain triglycerides, and soy isoflavones, wherein the body fat reducing agents are administered to the animal in amounts of from about 0.001 to about 1000 mg/kg/day; and
    one or more insulin sensitivity enhancing agents selected from the group consisting of chromium, chromium picolinate, cinnamon, cinnamon extract, polyphenols from cinnamon and witch hazel, coffee berry extract, chlorogenic acid, caffeic acid, a source of zinc, and grape seed extract, wherein the insulin sensitivity enhancing agents are administered to the animal in amounts of from about 0.001 to about 1000 mg/kg/day,
    wherein the combination excludes anti-inflammatory agents of omega-3 fatty acids and curcumin.

2. The method of claim 1, wherein the one or more antioxidants includes vitamin E, vitamin C, alpha-carotene, beta-carotene, lutein, zeaxanthin, cryptoxanthin, selenium, and lycopene; wherein the one or more insulin sensitivity enhancing agents include chromium, grape seed extract, and zinc; wherein the one or more body fat reducing agents include CLA, carnitine, and acetyl-carnitine; and the one or more anti-glycation agents include carnosine.

3. The method of claim 1, wherein the antioxidants are administered to the animal in amounts of from about 0.001 to about 10 grams per day.

4. The method of claim 1, wherein the anti-glycation agents are administered to the animal in amounts of from about 0.01 to about 10 grams per day.

5. The method of claim 1, wherein the body fat reducing agents are administered to the animal in amounts of from about 0.01 to about 10 grams per day.

6. The method of claim 1, wherein the insulin sensitivity enhancing agents are administered to the animal in amounts of from about 0.01 to about 10 grams per day.

* * * * *